US00PP36834P3

(12) United States Plant Patent
Olesen

(10) Patent No.: US PP36,834 P3
(45) Date of Patent: Jul. 22, 2025

(54) ROSE PLANT NAMED 'Poulpar136'

(50) Latin Name: *Rosa hybrida*
Varietal Denomination: Poulpar136

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,181

(22) Filed: Sep. 5, 2024

(65) Prior Publication Data

US 2025/0107462 P1 Mar. 27, 2025

(30) Foreign Application Priority Data

Sep. 22, 2023 (QZ) ..... PBR 2023/1979

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116, 121, 122
CPC ..... A01H 6/749; A01H 5/02
See application file for complete search history.

*Primary Examiner* — Keith O. Robinson

(57) ABSTRACT

A new garden rose plant of the Miniature class which has abundant, red-purple flowers and attractive foliage. This new and distinct variety has shown to be uniform and stable in the resulting generations from asexual propagation.

2 Drawing Sheets

Botanical designation: *Rosa hybrida.*

Variety denomination: 'Poulpar136'.

This application claims priority to Plant Breeder's Rights Application Number 2023/1979, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2019 and the resulting seeds were planted in a controlled environment in Fredensborg, Denmark. The new variety, named 'Poulpar136', originated as a single seedling from the stated cross.

The new variety may be distinguished from its male pollen parent and female seed parent primarily by the following characteristics. The male pollen parent plant has dark red flowers while the new variety has deep pink flowers. The female seed parent plant has medium pink flowers while the new variety has red-purple flowers.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance.

This combination of qualities is not present in previously available commercial cultivars of this type, known to the inventor, and distinguish 'Poulpar136' from all other varieties of which we are aware.

As part of the rose development program, Mogens N. Olesen germinated the seeds from the aforementioned hybridization during winter of 2019 and conducted evaluations on the resulting seedlings in a controlled environment in Fredensborg, Denmark. 'Poulpar136' was selected in the spring of 2020 by the inventor as a single plant from the progeny of the aforementioned hybridization.

Asexual reproduction of 'Poulpar136' by rooted cuttings was first done by Mogens N. Olesen in the nursery in Fredensborg, Denmark in July, 2020. This initial and other subsequent asexual propagations conducted in controlled environments have demonstrated that the characteristics of 'Poulpar136' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar136'.

Specifically illustrated in FIG. 1 of the drawings are open flowers at various stages of development viewed from above, a side view of open flower, petals detached revealing reproductive flower parts, sepals detached revealing the receptacle.

Figure 1:
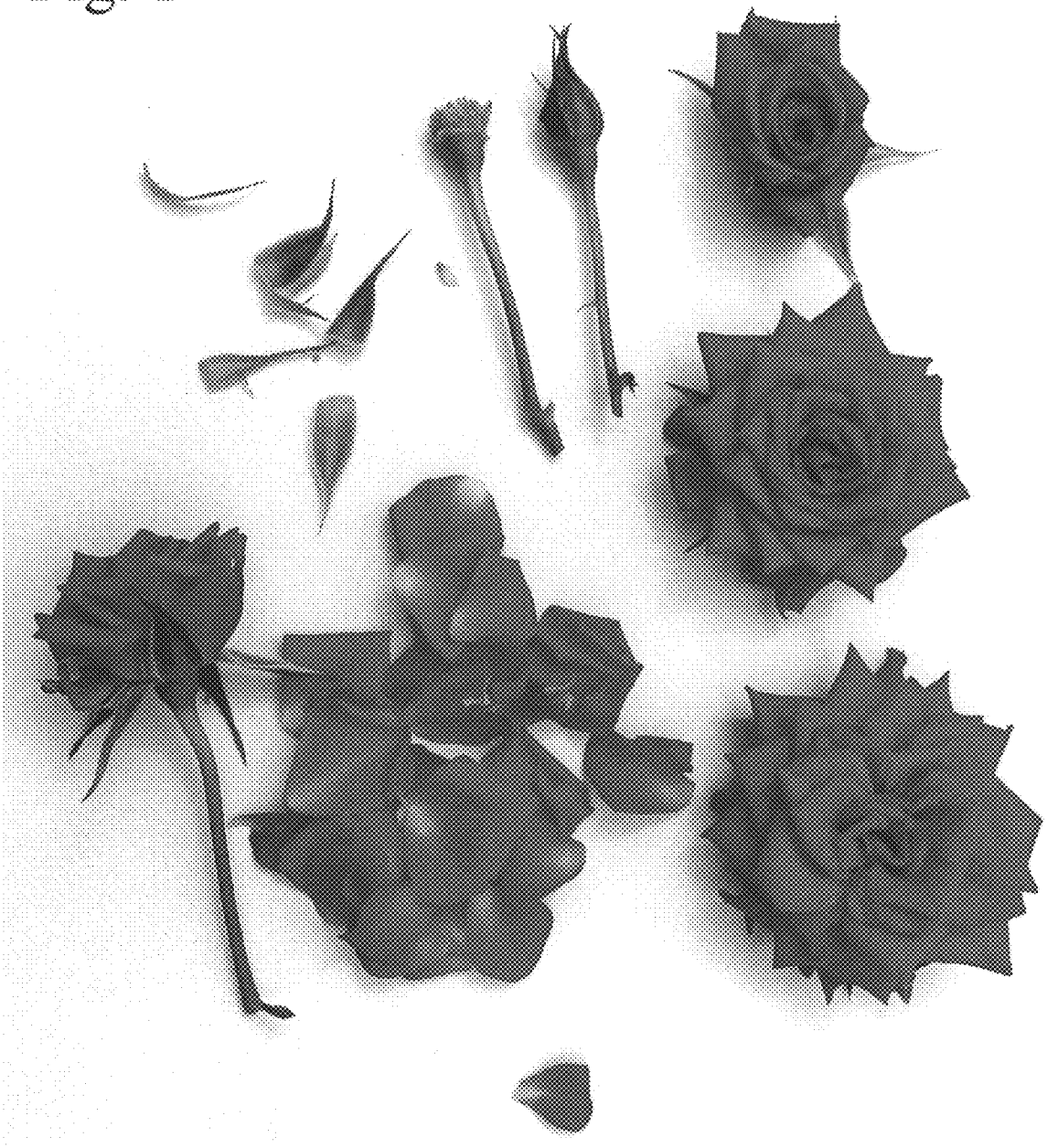
Figure 2:
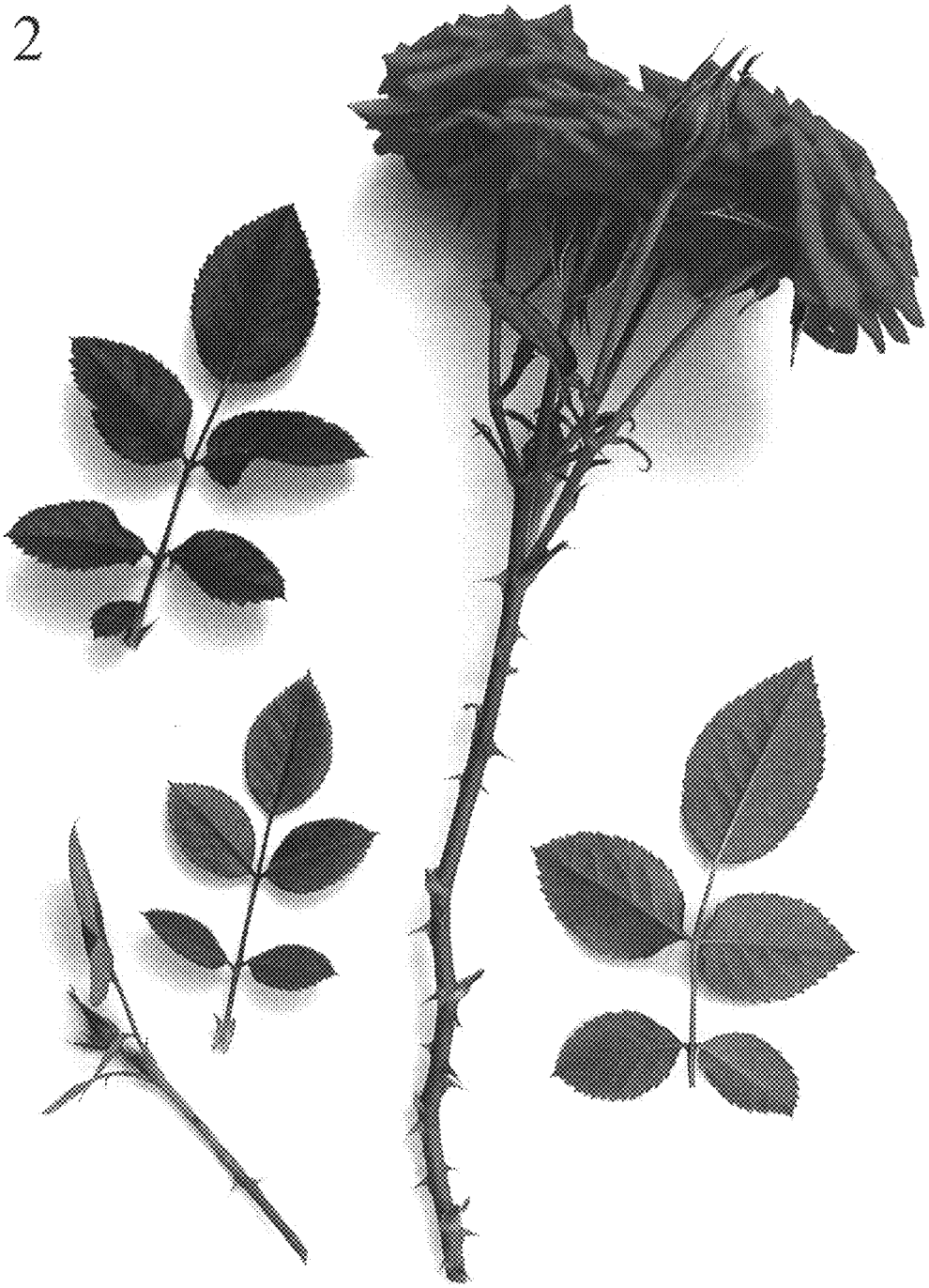

Specifically illustrated in FIG. 2 of the drawings are a cluster of flowers on a bare stem exhibiting prickles, juvenile growth and mature leaves. Plants shown are 3 months old.

DETAILED DESCRIPTION OF THE VARIETY

The following is a description of 'Poulpar136', as observed in its growth in a glasshouse nursery in Odense Denmark. Observed plants are 3 months of age, and were grown on their own roots in 23 cm pots. Color references are made using The Royal Horticultural Society (London, England) Colour Chart, 2001, except where common terms of color are used.

For a comparison, several physical characteristics of the rose variety 'Poulpar097', U.S. Plant Pat. No. 29,120 are compared to the claimed plant. While 'Poulpar136' has 40 flower petals, 'Poulpar097' has 45 flower petals. The claimed plant has a flower diameter of 50 mm while 'Poulpar097' has a flower diameter of 65 mm. Open flowers of 'Poulpar136' are generally Red-Purple Group N57A in color while 'Poulpar097' has a general tonality of Red-Purple Group N57C splashed with Red-Purple Group 63C.

FLOWER AND FLOWER BUD

Blooming habit: Continuous.

Flower bud:

*Size.*—Upon opening, 23 mm in length from base of receptacle to end of bud. Bud diameter is 10 mm.

*Bud form.*—Ovoid.

*Bud color.*—As sepals divide petals are Red Purple 61B.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have light to no foliaceous appendages on three of the five sepals.

*Sepal size.*—About 20 mm long, 9 mm wide.

*Receptacle.*—Texture: Smooth. Size: 7 mm in height, 5 mm wide. Color: Yellow-Green Group 144A. Shape: Funnel.

*Pedicel.*—Surface: Smooth. Length: 32 mm. Diameter: 2.5 mm on average. Color: Yellow-Green Group 144A. Strength: Strong.

*Peduncle.*—Length: 30 mm. Diameter: About 2 or 3 mm. Color: Yellow-Green Group 144A. Texture: Smooth.

Flower bud development: Flower buds are borne in clusters of 5 flower buds per stem. Development as a panicle.

Flower bloom:

*Fragrance.*—Moderate floral.

*Duration.*—The blooms have a duration on the plant of approximately 28 days. Petals fall cleanly away from plant after flowers have fully matured.

*Size.*—Flower diameter is about 50 mm when open. Flower depth is 20 mm.

*Flower shape.*—Star shaped from above. High centered double flower with tightly closed center.

*Shape of flower, side view.*—The upper portion is convex. The lower portion is flat concave.

Petalage: Under normal conditions, flowers have about 40 petals.

General tonality of flower: Open flowers are Red-Purple Group N57A. After 10 days Red-Purple Group N57C.

Petal color:

*Upon opening, outer and inner petals.*—Upper surface: Red-Purple Group N57A with shades of White Group 155C at basal zone along with the yellow petal spot. Lower surface: Red-Purple Group 58B with light intonations of White Group N155A at the basal zone along with the yellow petal spot.

*Basal petal spots, upon opening.*—Upper surface: Yellow Group 6B. Lower surface: Yellow Group 4C.

*After opening, outer and inner petals.*—Upper surface: Red-Purple Group N57A with shades of White Group 155C at basal zone along with the yellow petal spot. Lower surface: Red-Purple Group 58B with light intonations of White Group N155A at the basal zone along with the yellow petal spot.

*Basal petal spots, after opening.*—Upper surface: Yellow Group 6B. Lower surface: Yellow Group 4C.

Petals:

*Petal reflex.*—Bilateral strong reflexed.

*Margin.*—Entire and uniform. Moderate undulations.

*Shape.*—Broad and elliptic. Apex shape: Rounded. Base shape: Acute.

*Size.*—About 26 mm (l)×26 mm (w).

*Texture.*—Smooth.

*Thickness.*—Average.

Petaloids:

*Size.*—15 mm (l) by 9 mm (w).

*Quantity.*—3 to 4.

*Shape.*—Elliptical with an acute base and rounded apices.

*Color.*—Upper surface is Red-Purple Group N57A. Underneath, Red-Purple Group 61B. Petaloid basal petal spot is Yellow Group 6B on the upper surface and Yellow Group 4C on the lower surface.

Reproductive flower parts:

*Pollen.*—None observed.

*Anthers.*—Size: 2 mm in length. Color: Yellow-Orange Group 14D. Quantity: 35 on average.

*Filaments.*—Color: Yellow-Orange Group 14C and Yellow-Orange Group 23B. Length: 3 mm.

*Pistils.*—Length: 6 mm. Quantity: 25 on average.

*Stigmas.*—Color: Greyed-Red Group 179D.

*Styles.*—Color: Green-White Group 157A.

*Location of stigmas.*—Superior in location relative to the length of the filaments and the height of the anthers.

*Hips.*—None Observed.

PLANT

Plant growth: Miniature. Plants are 35 cm in height, and 48 cm wide.

Stems:

*Color of juvenile growth.*—Yellow-Green Group 144B.

*Color of mature growth.*—Yellow-Green Group 144A.

*Length.*—Canes are about 20 cm from the base of the plant to the flowering portion.

*Diameter.*—About 3.5 mm.

*Internodes.*—On mature canes about 22 mm between nodes.

*Surface texture.*—Young wood: Smooth. Older wood: Smooth.

Long prickles:

*Incidence.*—About 12 prickles per 10 cm of stem.

*Size.*—Average length of prickles on mature stems is 6 mm.

*Shape.*—Upper portion is linear. Lower portion is concave.

*Color.*—Juvenile prickles: Greyed-Yellow Group 160A. Mature prickles: Greyed-Orange N170C.

Plant foliage:

*Compound leaf.*—110 mm (l)×55 mm (w).

*Quantity.*—3 or 4 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 146B.

Plant leaves and leaflets:

*Stipules.*—Size: 8 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 15 mm. Diameter: 1.5 mm. Upper surface color: Yellow-Green Group 144A. Lower surface color: Yellow-Green Group 144A.

*Rachis.*—Length: About 50 mm. Upper surface color: Yellow-Green Group 144A. Lower surface color: Yellow-Green Group 144A. Lower surface texture: Rough with small prickles, White Group 155A and intonations of Greyed-Red Group 181D.

*Leaflet.*—Quantity: Normally 5 leaflets. Margins: Serrated. Size: Terminal leaflets are about 40 mm long, 26 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpar136' substantially as described and illustrated herein.

* * * * *